United States Patent
Guerrera et al.

(10) Patent No.: US 11,241,234 B2
(45) Date of Patent: Feb. 8, 2022

(54) ANVIL ASSEMBLY WITH SELF-RETAINING BACKUP MEMBER

(71) Applicant: Covidien LP, Mansfield, MA (US)

(72) Inventors: Joseph Guerrera, Watertown, CT (US); Anthony Sgroi, Jr., Wallingford, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 52 days.

(21) Appl. No.: 16/451,118

(22) Filed: Jun. 25, 2019

(65) Prior Publication Data
US 2020/0054336 A1 Feb. 20, 2020

Related U.S. Application Data

(60) Provisional application No. 62/718,486, filed on Aug. 14, 2018.

(51) Int. Cl.
 *A61B 17/068* (2006.01)
 *A61B 17/115* (2006.01)
 *A61B 17/00* (2006.01)
 *A61B 17/072* (2006.01)

(52) U.S. Cl.
 CPC . *A61B 17/1155* (2013.01); *A61B 2017/00314* (2013.01); *A61B 2017/07257* (2013.01); *A61B 2017/07271* (2013.01); *A61B 2017/07285* (2013.01)

(58) Field of Classification Search
 CPC .......... A61B 17/1155; A61B 17/32053; A61B 2017/07257
 See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Eyamindae C Jallow
(74) *Attorney, Agent, or Firm* — Carter, DeLuca & Farrell LLP

(57) ABSTRACT

An anvil assembly includes an anvil head pivotally secured to a center rod assembly and a self-retaining backup member disposed with the anvil head assembly. The backup member is moveable between a retracted position in which the anvil head assembly is retained in an operative position and an advanced position in which the anvil head assembly is moveable to a tilted position. The backup member includes a pair of opposed snap tabs for retaining the backup member in its advanced position, a plurality of fingers for engaging a frangible ring of a retaining member, and retaining features for securing a cut ring assembly to the backup member.

18 Claims, 12 Drawing Sheets

(56) References Cited

U.S. PATENT DOCUMENTS

| | | |
|---|---|---|
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Mien et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |

(56) References Cited

U.S. PATENT DOCUMENTS

| | | |
|---|---|---|
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |

(56) References Cited

U.S. PATENT DOCUMENTS

| | | |
|---|---|---|
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,540,132 B2 | 9/2013 | Marczyk et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,789,737 B2 | 7/2014 | Hodgkinson et al. |
| 8,806,973 B2 | 8/2014 | Ross et al. |
| 9,055,943 B2 | 6/2015 | Zemlok et al. |
| 9,247,940 B2 | 2/2016 | Whitman et al. |
| 9,554,802 B2 | 1/2017 | Williams et al. |
| 2003/0111507 A1 | 6/2003 | Nunez |
| 2004/0073090 A1 | 4/2004 | Butler et al. |
| 2005/0006433 A1* | 1/2005 | Milliman ............ A61B 17/1114 227/176.1 |
| 2005/0051597 A1 | 3/2005 | Toledano |
| 2005/0107813 A1 | 5/2005 | Garcia |
| 2005/0116009 A1* | 6/2005 | Milliman ............ A61B 17/072 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1* | 1/2011 | Levine ................ A61B 17/115 227/179.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |

(56) References Cited

U.S. PATENT DOCUMENTS

| | | |
|---|---|---|
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0014392 A1 | 1/2015 | Williams et al. |
| 2015/0129635 A1* | 5/2015 | Williams ............ A61B 17/1155 227/177.1 |
| 2016/0143641 A1 | 5/2016 | Sapienza et al. |
| 2016/0157855 A1* | 6/2016 | Williams ............ A61B 17/1155 227/180.1 |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0206846 A1* | 7/2018 | Guerrera ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

ANVIL ASSEMBLY WITH SELF-RETAINING BACKUP MEMBER

CROSS-REFERENCE TO RELATED APPLICATIONS

This application claims the benefit of and priority to U.S. Provisional Patent Application Ser. No. 62/718,486 filed Aug. 14, 2018, the entire disclosure of which is incorporated by reference herein.

BACKGROUND

Technical Field

The present disclosure relates generally to an anvil assembly having a tiltable head which is suitable for use with a circular anastomosis surgical stapling device. More specifically, the present disclosure relates to a tiltable anvil assembly having a self-retaining backup member.

Background of Related Art

Circular anastomosis surgical stapling devices which include an anvil assembly having a tiltable anvil head assembly are known in the art. An example of such a circular anastomosis surgical stapling device and tiltable anvil assembly is disclosed in commonly owned U.S. Pat. No. 7,364,060 ("the '060 patent"). A further example of a tiltable anvil assembly is disclosed in commonly owned U.S. Pat. No. 8,540,132 ("the '132 patent"). The contents of the '060 and '132 patents are incorporated herein by reference in their entirety. The anvil assembly described in the '132 patent includes a backup member located within the anvil assembly positioned to prevent tilting of the anvil head assembly of the anvil assembly prior to firing of the surgical stapling device. Upon firing of the surgical stapling device, a knife blade of the surgical stapling device engages and moves the backup member to a position which allows the anvil head assembly to tilt upon retraction of the knife blade. If the backup member sticks to the knife blade upon retraction of the knife blade, the backup member may return to its position preventing tilting of the anvil head assembly. When this occurs, the anvil head assembly will not tilt.

In order to maintain the backup member in a distal position post firing of the surgical stapling device, the anvil assembly described in the '132 patent includes a cam latch member that is pivoted into engagement with the backup member post firing to prevent retraction of the backup member. Providing a backup member that remains in the distal position post firing eliminates the need for a cam latch member, thereby reducing the number of components and reducing the manufacturing costs of the anvil assembly.

Therefore, it would be beneficial to provide an anvil assembly with a self-retaining backup member that maintains itself in the distal position post firing of the stapling assembly.

SUMMARY

Accordingly, an anvil assembly including a self-retaining backup member is provided. The anvil assembly includes a center rod assembly including an anvil center rod defining a longitudinal axis and having a proximal portion and a distal portion and an anvil head assembly pivotally secured to the distal portion of the anvil center rod. The anvil head assembly includes a housing, a backup member, a cut ring assembly, and a retainer member. The housing defines a recess and includes a post centrally disposed within the recess. The anvil head assembly is pivotal in relation to the anvil center rod from an operative position in which the longitudinal axis of the anvil center rod is aligned with a longitudinal axis of the post to a tilted position in which the longitudinal axis of the anvil center rod and the longitudinal axis of the post define an acute angle. The backup member and cut ring assembly are supported about the post and movable between retracted and advanced positions. The retainer member is positioned about the post to retain the backup member in its retracted position until a predetermined force is applied to the retainer member by the backup member. When in its retracted position, the backup member is positioned to engage the center rod to retain the anvil head assembly in the operative position. When in its advanced position, the backup member is positioned to permit pivotal movement of the anvil head assembly to the tilted position. The backup member is configured to retain the cut ring assembly in its advanced position.

In embodiments, the housing includes a tissue contact surface defining a plurality of staple deforming pockets. The retainer member may include a frangible portion and a body portion. Separation of the frangible portion from the body portion may permit the backup member to move to from its retracted position to its advanced position.

The backup member may include retaining features for securing the cut ring assembly to the backup member. The post may define opposed retaining features and the backup member may include opposed snap tabs. The snap tabs may engage the retaining features when the backup member is in the advanced position to secure the backup member in the advanced position. Proximal facing surfaces of the retaining features may be tapered to facilitate passage of the snap tabs over the retaining features as the backup member moves to its advanced position. Distal facing surfaces of the retaining features may form a stop surface configured to engage the snap tabs of the backup member to retain the backup member in its advanced position.

In some embodiments, the backup member includes a plurality of fingers that engage the frangible portion of the retainer member. The backup member may include raised flanges. The cut ring assembly may be securely supported about the raised flanges. The center rod assembly may include a plunger and a plunger spring. The plunger spring may be positioned to urge the plunger towards the anvil head assembly to urge the anvil head assembly from the operative position towards the tilted position.

The backup member may include a pair of opposed engagement tabs positioned to engage the proximal portion of the anvil center rod when the backup member is in its retracted position. The anvil center rod may include a pair of spaced arms each having a distally facing flat. The distally facing flats may be positioned to engage the opposed engagement tabs of the backup member when the backup member is in its retracted position. The cut ring assembly may include an inner sleeve and a body. The inner sleeve and the body may each define a central opening. The inner sleeve may be secured within the central opening of the body. The central opening of the inner sleeve may be dimensioned to receive the raised flanges of the backup member. The cut ring assembly may include a base member that is positioned between a proximal surface of the body and a distal surface of the backup member. The backup member may be formed of metal.

BRIEF DESCRIPTION OF THE DRAWINGS

Various embodiments of the presently disclosed anvil assembly with self-retaining backup member are described herein below with reference to the drawings, wherein.

DETAILED DESCRIPTION OF EMBODIMENTS

Figure 1:
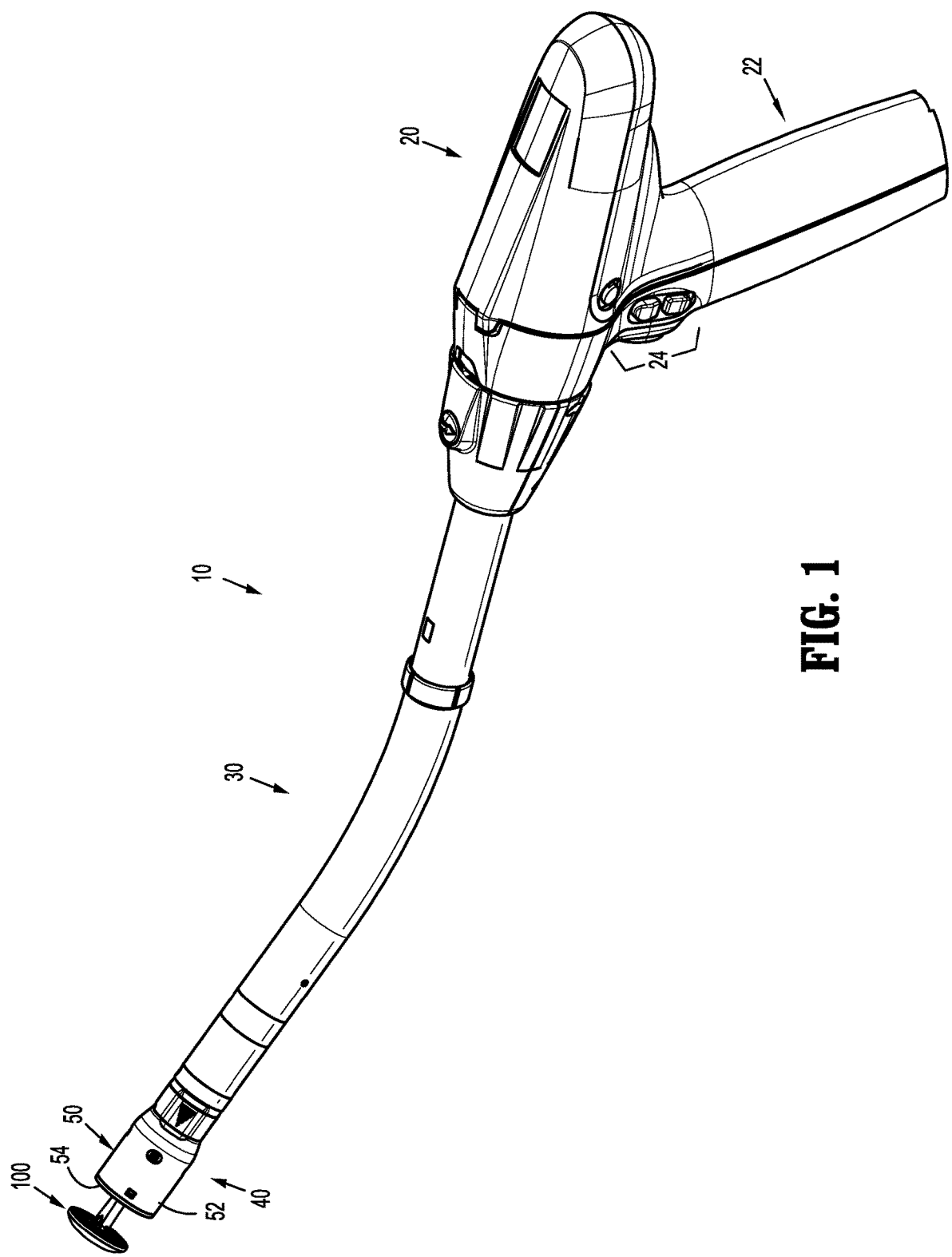
FIG. 1 is a side, perspective view of one embodiment of the presently disclosed surgical stapling device including an anvil assembly having a self-retaining backup member.

The presently disclosed surgical stapling device including a tiltable anvil assembly having a self-retaining backup member will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The presently disclosed surgical stapling device includes a handle or actuator assembly, an elongate body or adapter, and a tool assembly coupled to a distal portion of the adapter. The tool assembly includes a tiltable anvil assembly and a shell assembly. The anvil assembly includes a center rod that is releasably coupled to the adapter and an anvil head assembly that is pivotally coupled to the center rod. The anvil head assembly supports a cut ring assembly that is movable between a pre-fired or retracted position in which the cut ring assembly retains the anvil head assembly in an untilted or operative position and a second or advanced position in which the cut ring assembly is positioned to allow movement of the anvil head assembly to a tilted position. The anvil assembly also includes a retainer having a frangible portion that separates from a base portion to allow the cut ring assembly to move from the first position to the second position. In embodiments, the anvil head assembly includes a backup member that retains the cut ring assembly in the advanced position to allow the anvil head assembly to move to the tilted position and prevent retraction of the cut ring assembly.

Referring to FIG. 1, the presently disclosed surgical stapling device is shown generally as stapling device 10, and includes a handle or actuator assembly 20, an elongate body or adapter assembly 30, and a tool assembly 40. The handle assembly 20, as illustrated, is an electrically powered assembly and includes a grip 22 and actuation buttons 24 that can be depressed to actuate various functions of the stapling device 10 including approximation of the tool assembly 40 and firing of staples. In embodiments, the grip 22 supports a battery pack (not shown) which powers the handle assembly 20.

In embodiments, the adapter assembly 30 is releasably coupled to a distal portion of the handle assembly 20 and includes a plurality of drive mechanisms (not shown) that translate power from the handle assembly 20 to the tool assembly 40 in response to actuation of the actuation buttons 24 to effect operation, i.e., approximation and firing, of the tool assembly 40. The adapter assembly 30 also includes an anvil retainer (not shown) that extends from a distal portion of the adapter assembly 30 and is movable between retracted and advanced positions. U.S. Pat. Nos. 9,247,940, 9,055,943, and 8,806,973, and U.S. Publication No. 2015/0014392 disclose exemplary embodiments of powered handle assemblies and adapter assemblies and are incorporated herein by reference in their entirety. Alternately, the elongate body or adapter assembly 30 can be non-removably secured to the actuator assembly 20.

It is also envisioned that the actuator assembly 20 could be manually powered. Examples of manually powered handle assemblies are described in U.S. Pat. Nos. 8,1409,737, 8,424,535 ('535 patent) and U.S. Pat. No. 8,3100,295 which are incorporated herein in their entirety by reference.

Figure 14:
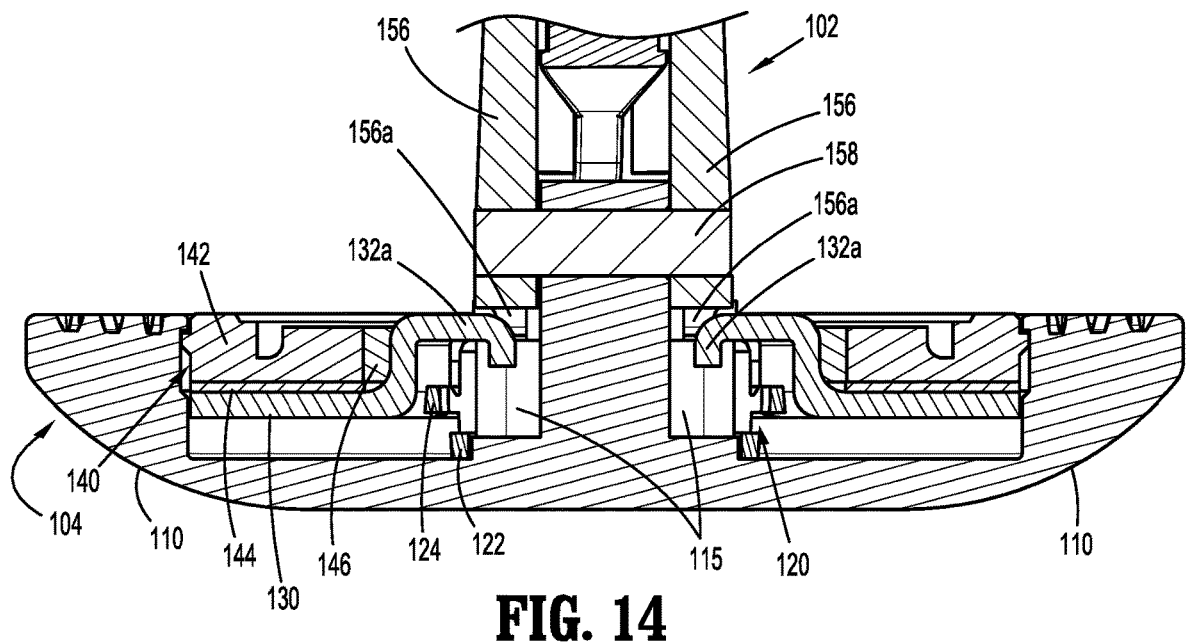
FIG. 14 is a cross-sectional view taken along line 14-14 shown in FIG. 2.
Figure 14A:
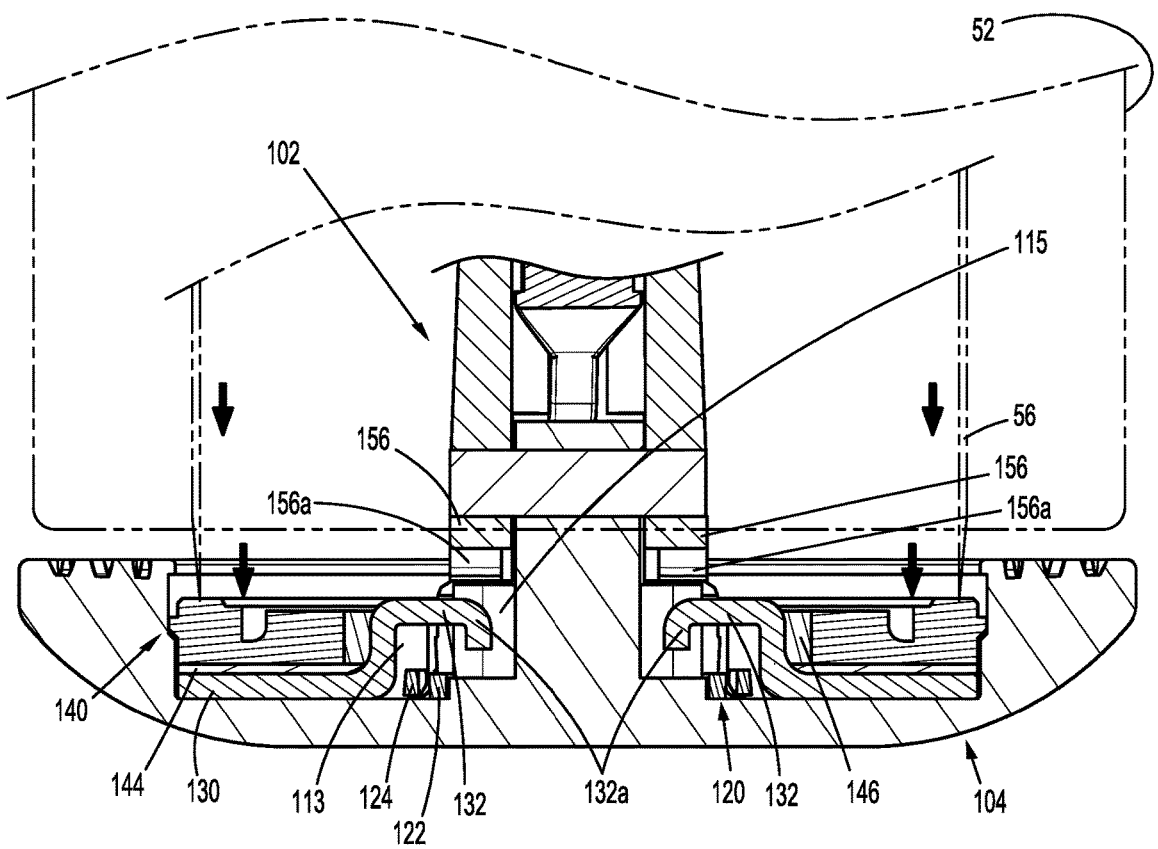
FIG. 14A is a cross-sectional view taken along line 14-14 shown in FIG. 2 with the cut ring assembly, the retainer member, and the backup member in a post-fired position.

The tool assembly 40 includes a shell assembly 50 and an anvil assembly 100. The shell assembly 50 includes a housing 52 that supports a staple cartridge 54 having an annular array of staple pockets (not shown) that support staples (not shown). The shell assembly 50 also includes components that facilitate firing of the staples from the staple cartridge 54 and an annular knife 56 (FIG. 14A; shown in phantom) that is movable from a retracted position recessed within the housing 52 to an advanced position extending into the anvil assembly 100. The '535 patent describes the components of a shell assembly suitable for use with the presently disclosed stapling device 10.

Figure 2:
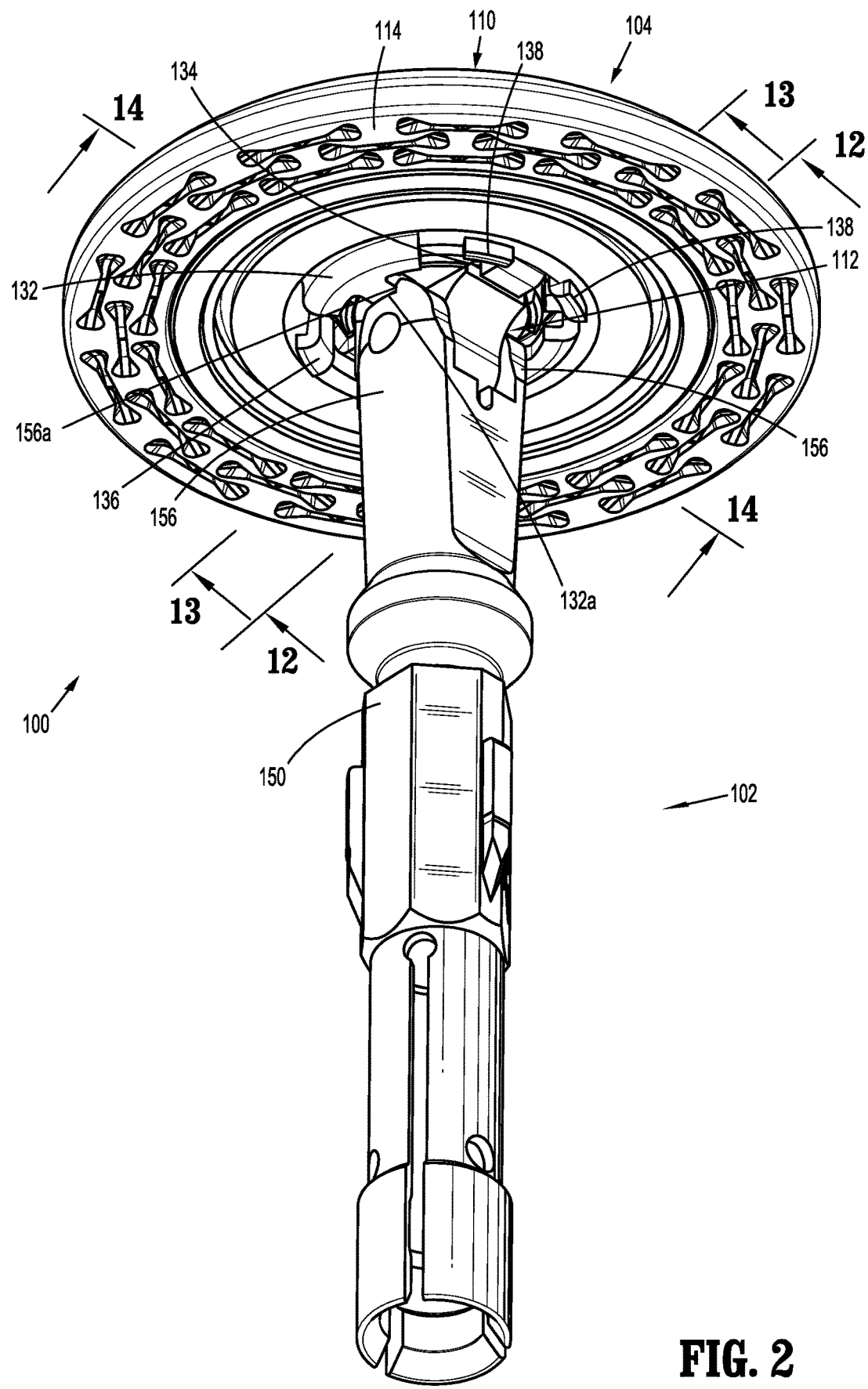
FIG. 2 is a perspective view of the anvil assembly shown in FIG. 1 with an anvil head assembly of the anvil assembly in an operative position.
Figure 3:
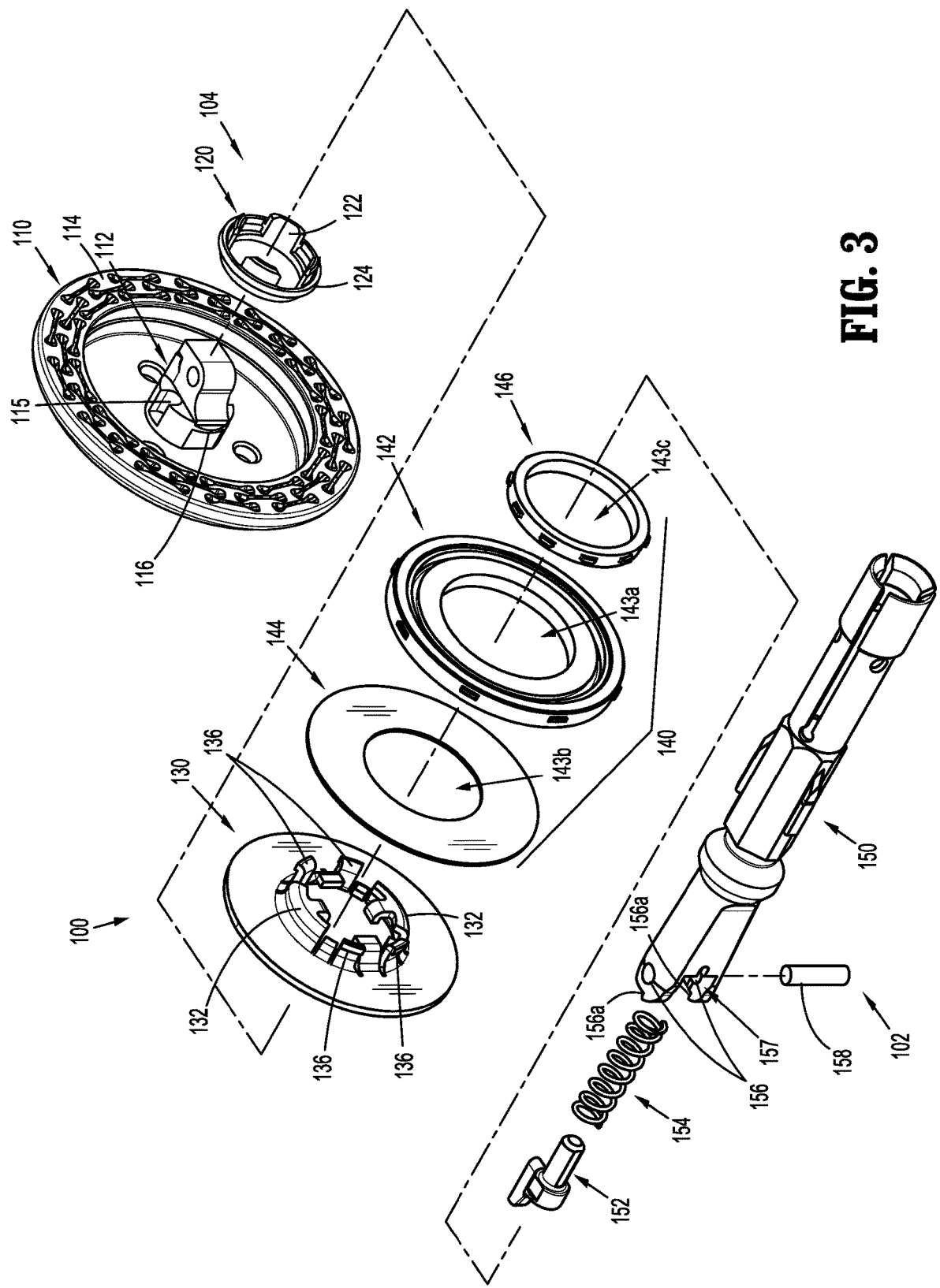
FIG. 3 is a side perspective view of the anvil assembly shown in FIG. 2 with parts separated.

Referring to FIGS. 2 and 3, the anvil assembly 100 includes an anvil center rod assembly 102 and an anvil head assembly 104 that is pivotally supported on a distal portion of the anvil center rod assembly 102. The anvil head assembly 104 includes a housing 110 including a post 112 and an anvil tissue contact surface 114, a retaining member 120, a backup member 130, and a cut ring assembly 140. In embodiments, the housing 110, the post 112, and the anvil tissue contact surface 114 are monolithically formed. Alternately, any one or all of the housing 110, the post 112, and the anvil tissue contact surface 114 may be formed separately and secured together using any known fastening technique including welding, crimping or the like.

Figure 4:
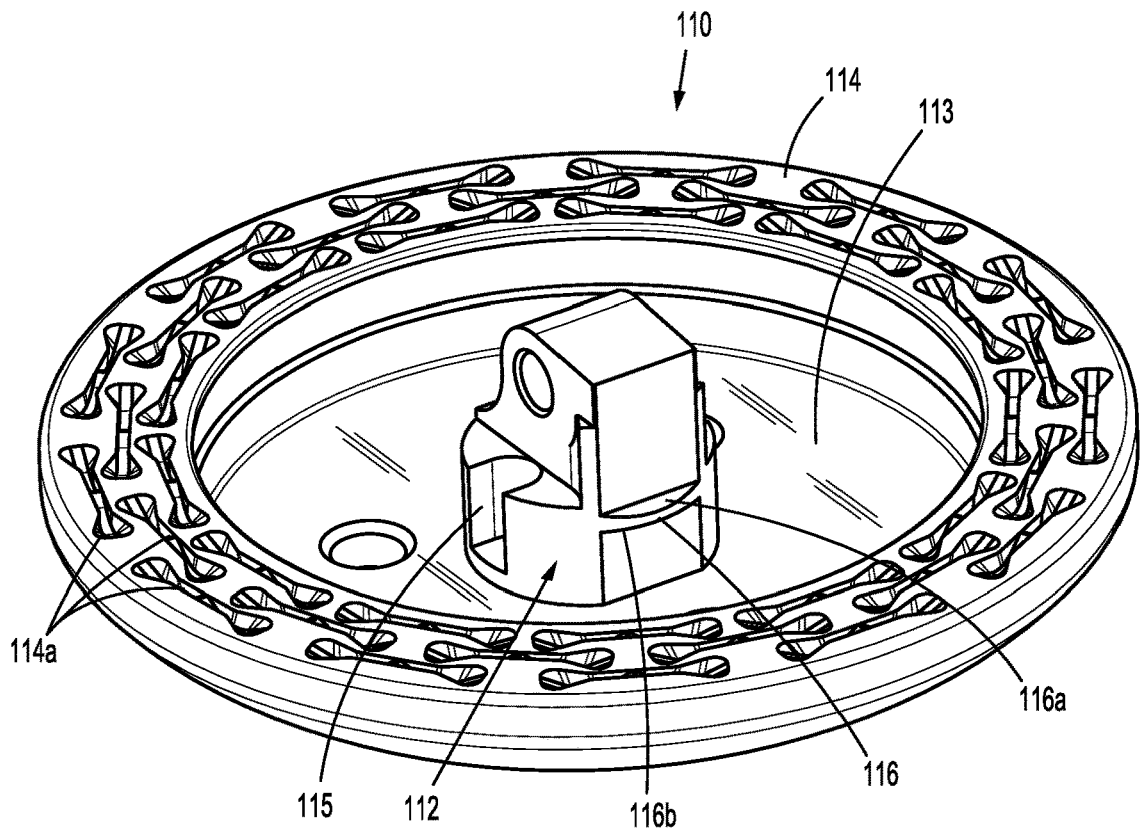
FIG. 4 is an enlarged, side perspective view of a housing of the anvil assembly shown in FIG. 2.
Figure 5:
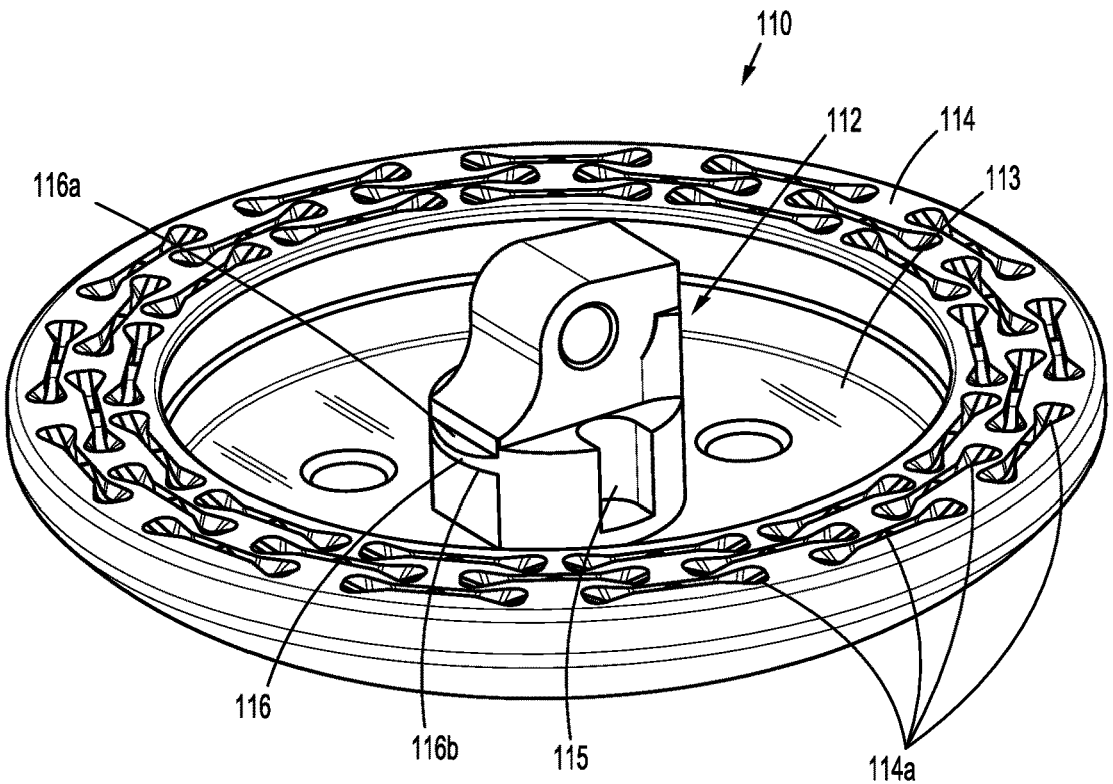
FIG. 5 is another enlarged, side perspective view of the housing shown in FIG. 4 rotated 90 degrees.

With additional reference to FIGS. 4 and 5, the housing 110 of the anvil head assembly 104 defines a recess 113 (FIG. 4) disposed between the post 112 and the tissue contact surface 114, with the post 112 centrally located within the recess 113. The tissue contact surface 114 of the housing 110 faces a tissue contacting surface (not shown) of the staple cartridge 54 (FIG. 1) and includes a plurality of staple deforming pockets 114a for receiving and deforming staples ejected from the staple cartridge 54.

Figure 6:
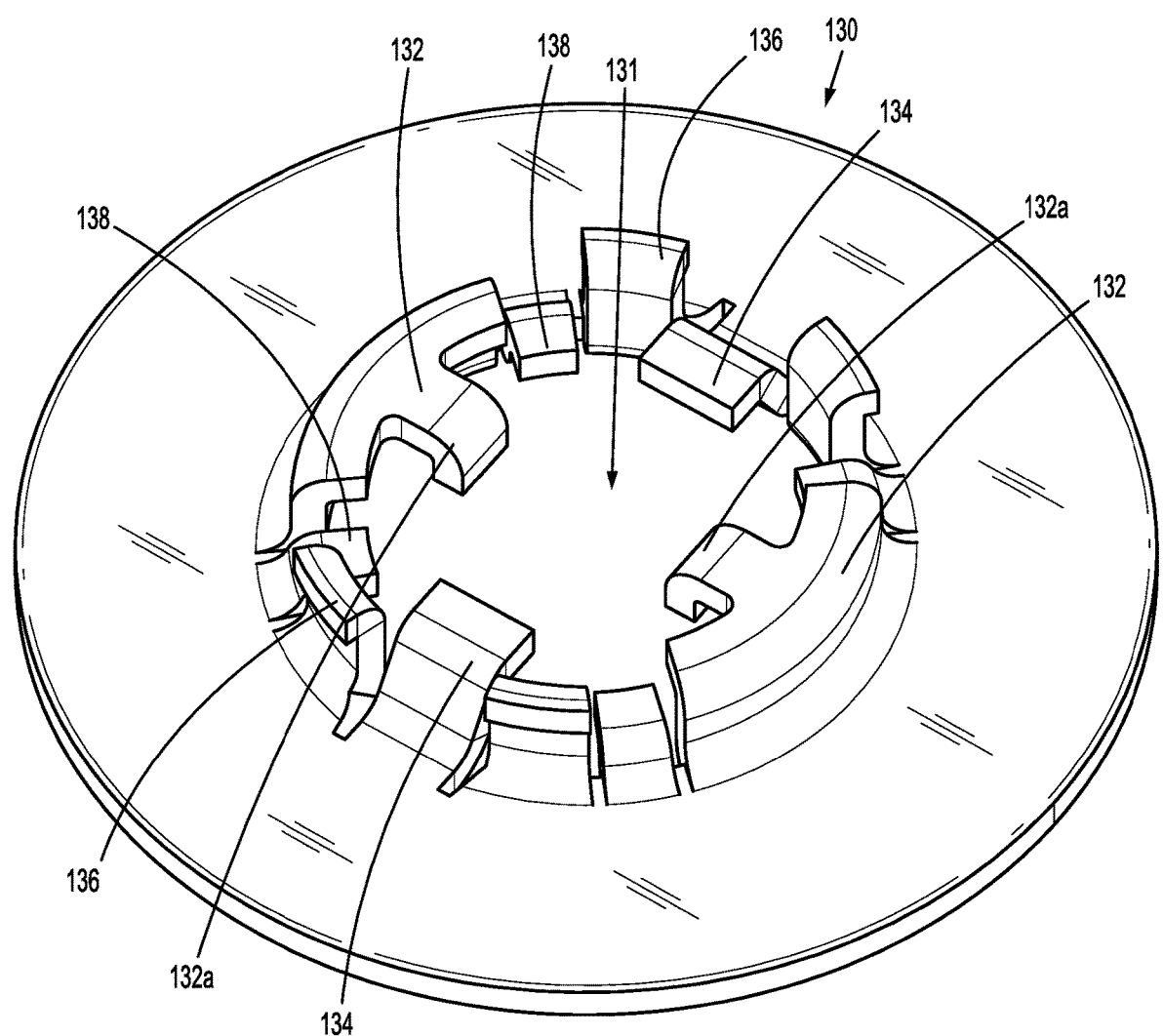
FIG. 6 is enlarged, perspective view from the distal end of a backup member of the anvil assembly shown in FIG. 2.

Referring also to FIG. 6, the post 112 of the anvil head assembly 104 defines a pair of opposed cutouts 115 and includes a pair of opposed retaining features 116. As described below, the cutouts 115 receive engagement tabs 132a of the backup member 130. The retaining features 116 engage snap tabs 134 of the backup member 130 when the backup member 130 is moved to a post-fired, advanced position to retain the backup member 130 in the advanced position. The retaining features 116 include an angled proximal facing surface 116a to facilitate passage of the snap tabs 134 of the backup member 130 over the retaining features 116 as the backup member 130 moves to an advanced position within the recess 113 as described below. The retaining features 116 further include a stop surface 116b configured to engage the snap tabs 134 of the backup member 130 when the backup member 130 is in the advanced position to retain the backup member 130 in the advanced position.

With reference to FIG. 3, the retainer member 120 of the anvil assembly 100 includes an annular body portion 122 and a frangible ring 124 supported on the annular body portion 120. The frangible ring 124 maintains the backup member 130 and the cut ring assembly 140 in a pre-fired, proximal position within the recess 113 until a predetermined force sufficient to fracture or separate the frangible ring 124 from the annular body portion 122 of the retainer member 120 is applied to the backup member 130 and cut ring assembly 140 by an annular knife 56 (FIG. 14A) of surgical stapling device 10 (FIG. 1). For a detailed description of the structure and function of an exemplary retainer member, please refer to U.S. Pat. No. 9,554,802 ("the '802 patent), the content of which is incorporated herein by reference in its entirety.

Figure 7:
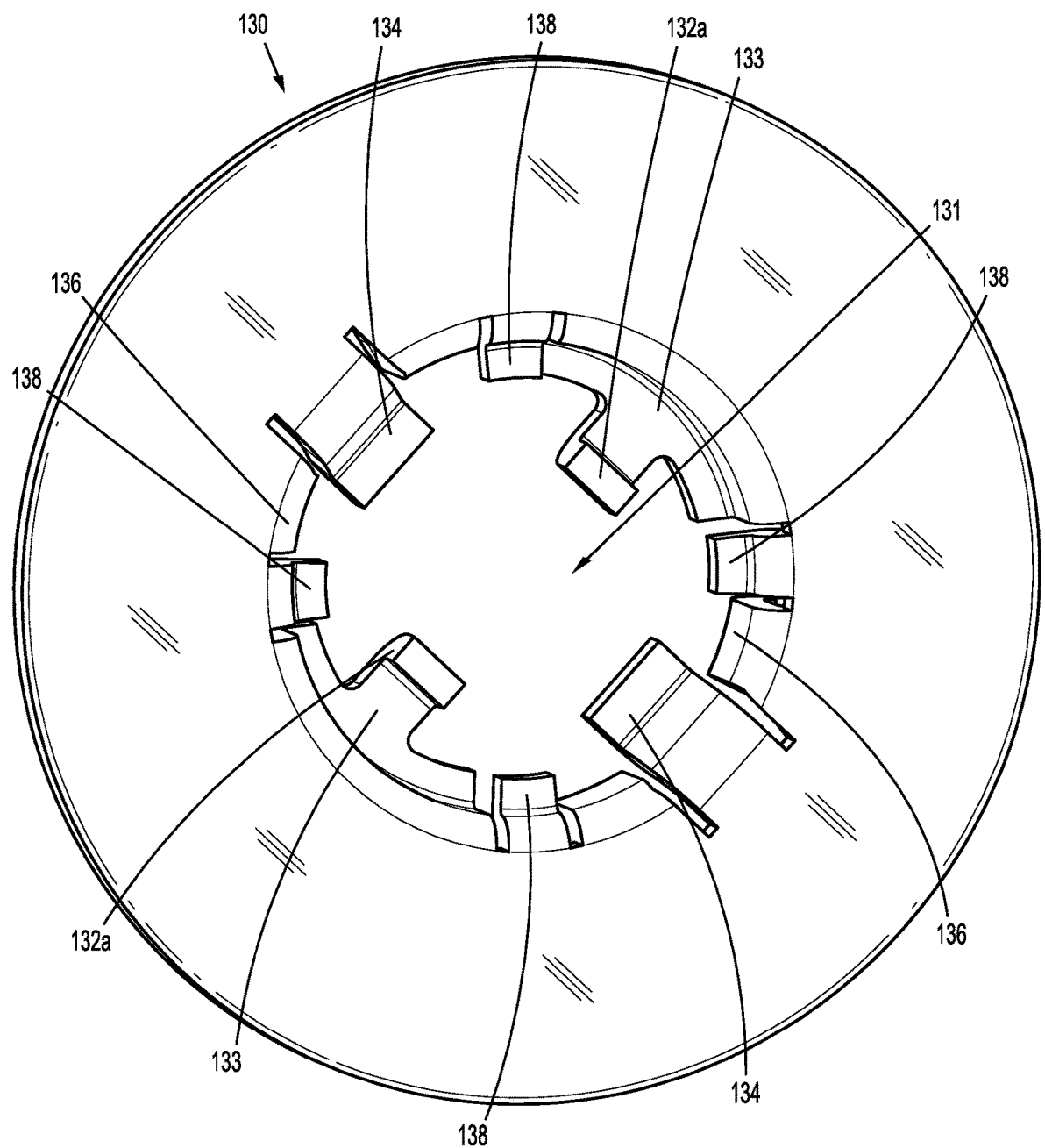
FIG. 7 is an enlarged view from the proximal end of the backup member shown in FIG. 6.
Figure 8:
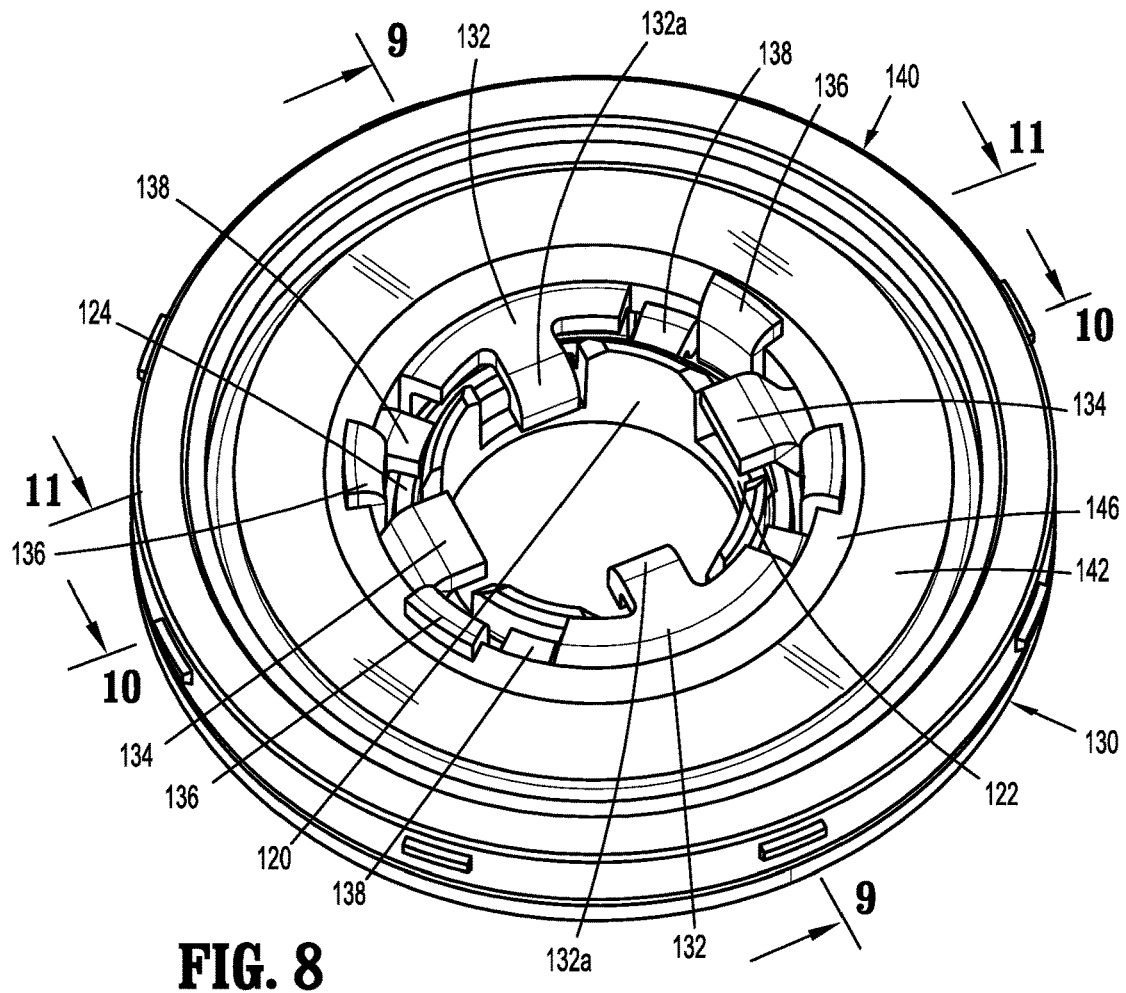
FIG. 8 is an enlarged perspective view from the distal end of a cut ring assembly, a retainer member, and the backup member of the anvil assembly shown in FIG. 2 in a pre-fired condition.
Figure 9:
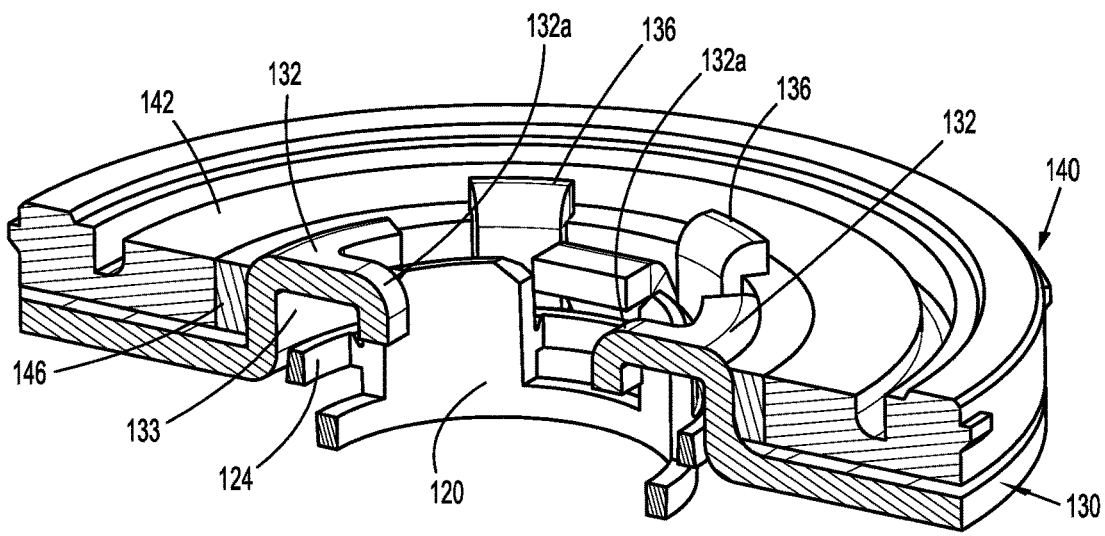
FIG. 9 is a cross-sectional view taken along line 9-9 shown in FIG. 8.
Figure 10:
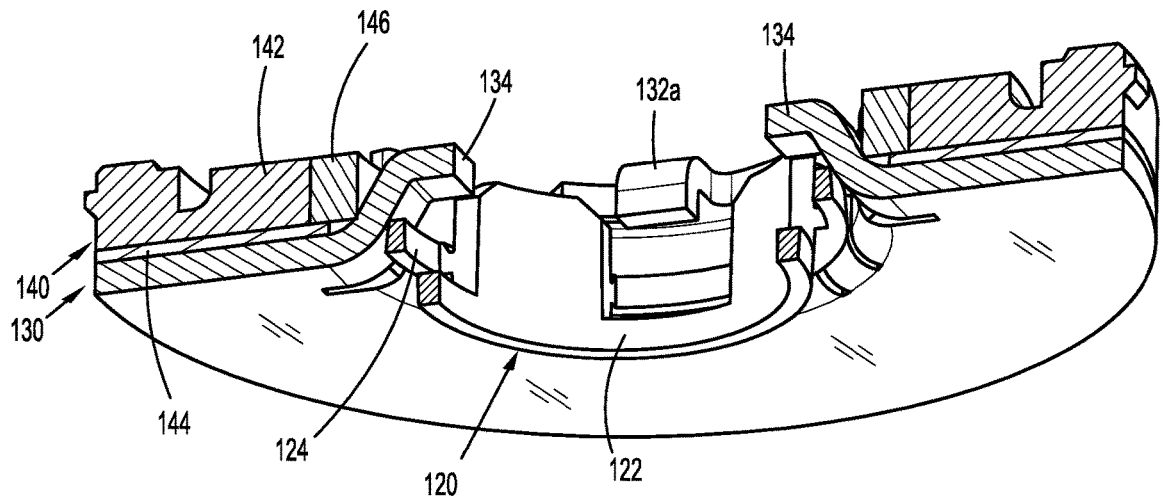
FIG. 10 is a cross-sectional view taken along line 10-10 shown in FIG. 8.
Figure 11:
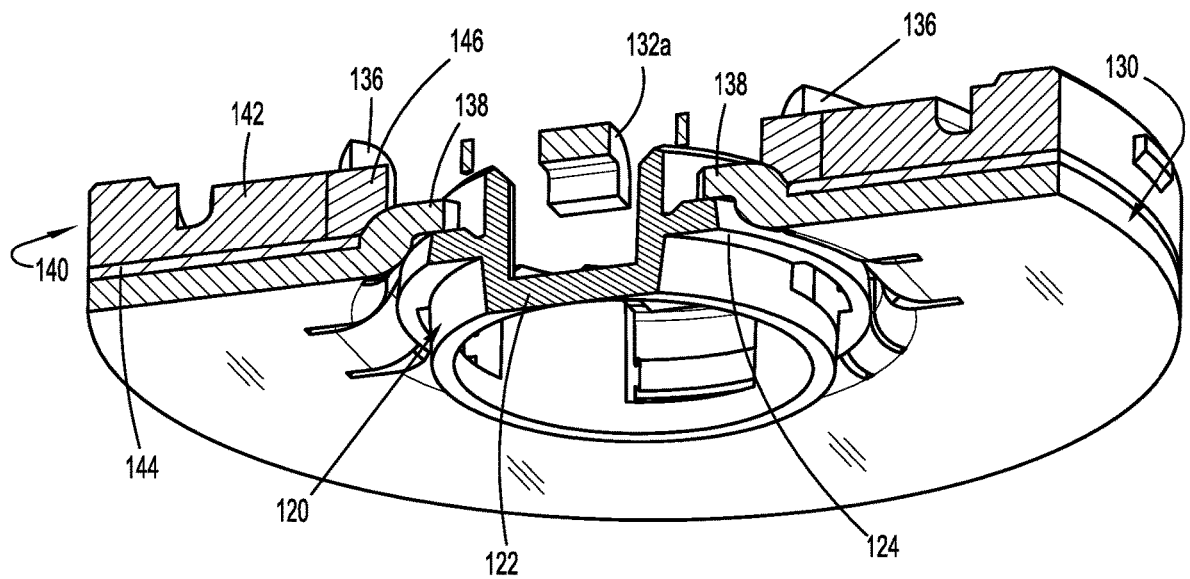
FIG. 11 is a cross-sectional view taken along line 11-11 shown in FIG. 8.

With particular reference to FIGS. 6 and 7, the backup member 130 of the anvil assembly 100 defines a central opening 131 that is dimensioned to receive the post 112 (FIG. 4) of the housing 110 of the anvil assembly 100. The central opening 131 is dimensioned to facilitate movement of the backup member 130 about the post 112 from the pre-fired, retracted position to the post-fired, advanced position within the recess 113 of the housing 110 as discussed in further detail below.

The backup member 130 includes a pair of raised flanges 132 that are positioned about the opening 131. The raised flanges 132 each define a recess 133 (FIG. 7) that accommodates the retaining member 130. The raised flanges 132 each include an engagement tab 132a that extends inwardly into central opening 131. The engagement tabs 132a are positioned to engage a distal portion of the center rod assembly 102 (FIG. 3) of the anvil assembly 100 when the backup member 130 is in its retracted position, to maintain the anvil head assembly 104 in the operative position. The engagement tabs 132a are positioned to be received within the cutouts 115 in the post 112 when the backup member 130 is moved to the post-fired, advanced position such that the engagement tabs 132a disengage from the distal portion of the center rod assembly 102 to allow the anvil head assembly 104 to pivot in relation to the center rod assembly 102. In embodiments, the engagement tabs 132a are bent ninety degrees (90°) to increase the structural integrity of the engagement tabs 132a.

The backup member 130 further includes snap tabs 134 for retaining the backup member 130 in the post-fired, advanced position. When the backup member 130 is moved to the advanced position, the snap tabs 134 are aligned with the retaining features 116 of the post 112 and engage the retaining features 116 of the post 112 when the backup member 130 is moved towards its retracted position. The backup member 130 also includes a plurality of cut ring retaining features 136 for retaining the cut ring assembly 140 in engagement with the backup member 130. In addition, the backup member 130 includes a plurality of retaining fingers 138 that engage the frangible ring 124 of the retainer member 120 as will be described below.

In embodiments, the backup member 130 is stamped from sheet metal, although other materials of construction and manufacturing techniques are envisioned. U.S. Pat. No. 8,540,132 which is incorporated herein in its entirety by reference discloses a tiltable anvil assembly that includes a backup member and cut ring assembly that are movably positioned about a post of an anvil head assembly.

With reference again to FIG. 3, in embodiments, the cut ring assembly 140 includes an annular body 142 formed of a first material, an annular base member 144 formed of a second material, and an annular inner sleeve 146. The body 142, the base member 144, and the sleeve 146 of the cut ring assembly 140 define openings 143a-c, respectively, that are configured to receive the raised flange 132 of the backup member 130. The sleeve 146 is secured to the body 142 and is positioned about the raised flange 132 of the backup member 130. The cut ring assembly 140 is secured the backup member 130 by the cut ring retaining features 136 of the backup member 130. In this manner, movement of the backup member 130 between its retracted and advanced positions causes corresponding movement of the cut ring assembly 140.

It is envisioned that a variety of cut ring assemblies can be included in the presently disclosed anvil head assembly. For example, the cut ring assembly need not include a sleeve and/or a base member 144.

For detailed description of the structure and operation of an exemplary cut ring assembly, please refer to commonly owned U.S. patent application Ser. No. 15/847,979, filed Dec. 20, 2017, the content of which is incorporated herein by reference in its entirety.

Figure 15:
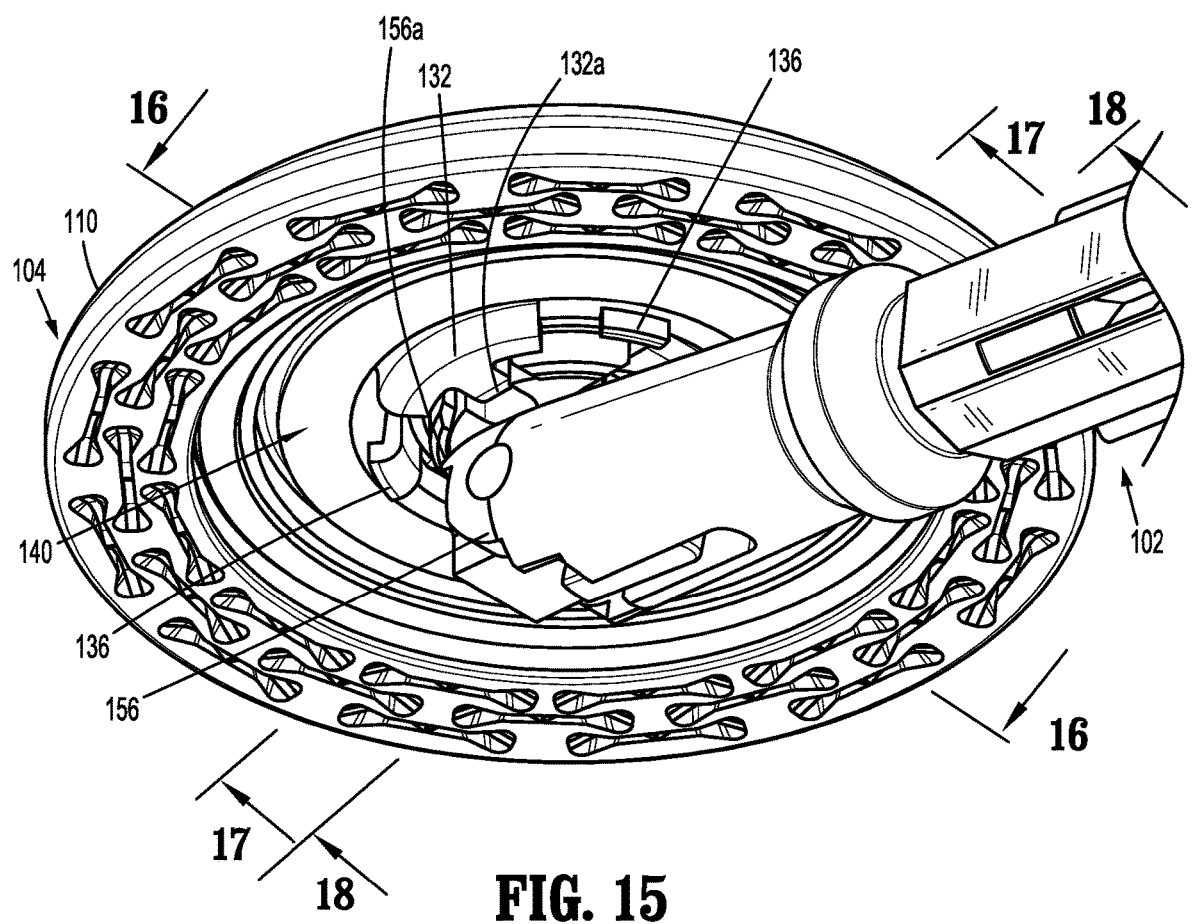
FIG. 15 is a side perspective view of the anvil head assembly shown in FIG. 2 in a tilted position.
Figure 16:
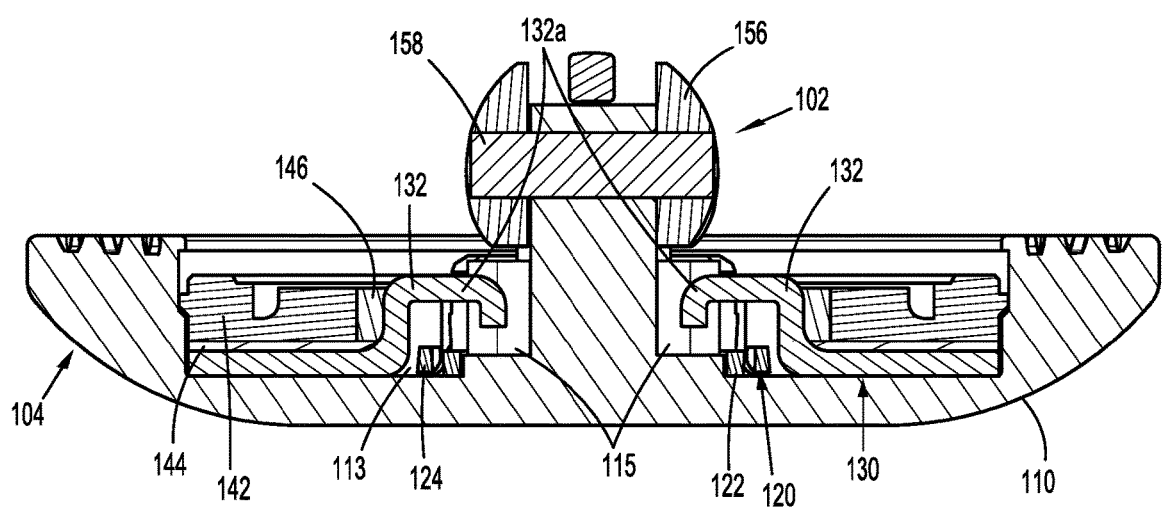
FIG. 16 is a cross-sectional view taken along line 16-16 shown in FIG. 15.
Figure 17:
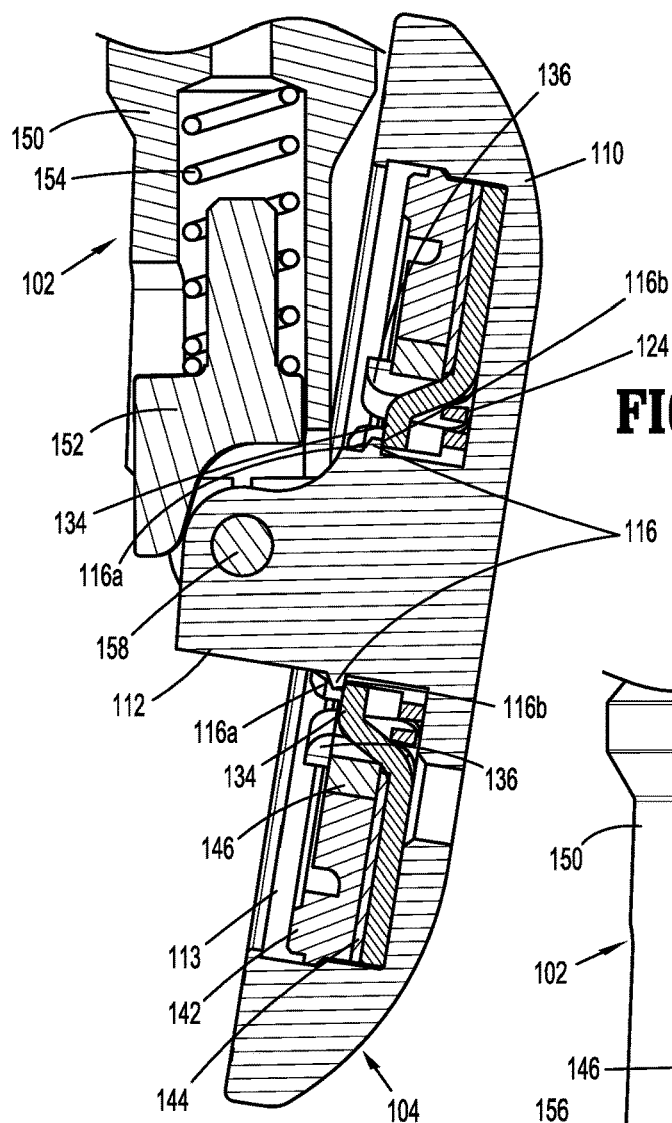
FIG. 17 is a cross-sectional view taken along line 17-17 shown in FIG. 15.
Figure 18:
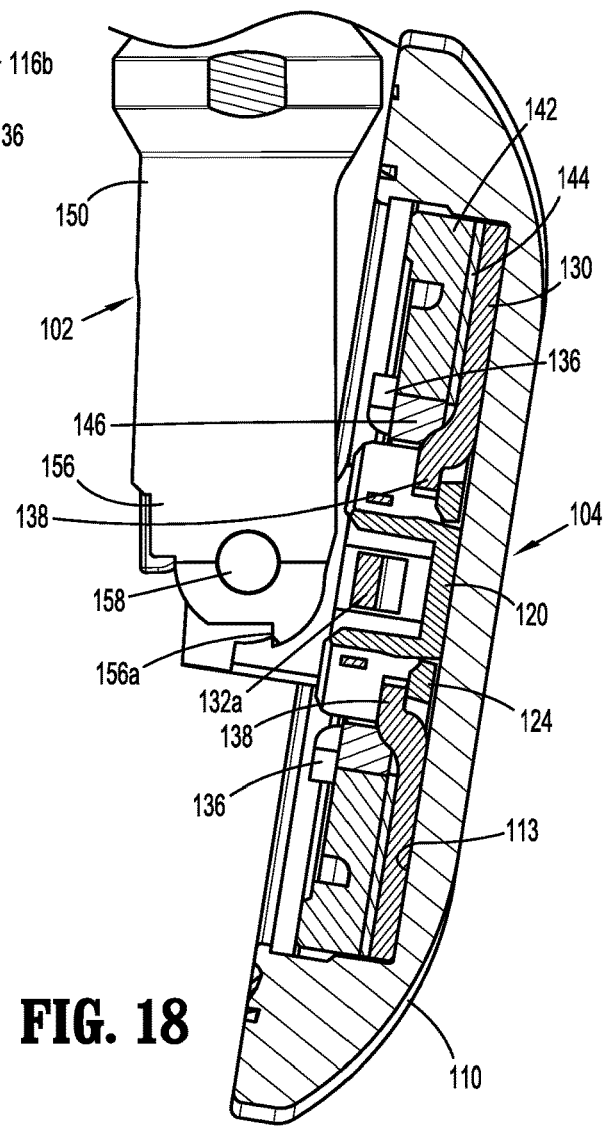
FIG. 18 is a cross-sectional view taken along line 18-18 shown in FIG. 15.

The center rod assembly 102 of the anvil assembly 100 includes a center rod 150, a plunger 152, and a plunger spring 154. A first end of center rod 150 includes a pair of spaced arms 156 that define a cavity 157 dimensioned to receive the post 112 of the anvil head assembly 104. The post 112 of anvil head assembly 104 is dimensioned to be positioned within cavity 157 defined between the spaced arms 156 of the center rod 150 and is pivotally secured to the center rod 150 by a pivot member 158. The anvil head assembly 104 is pivotable in relation to the center rod 150 between an operative position (FIG. 2) and a tilted position (FIG. 15). Each of the spaced arms 156 has distally facing flat 156a formed on the distal end of the center rod 150 that is dimensioned to engage the engagement tabs 132a of the backup member 130 when the backup member 130 is in its retracted position to releasably retain the anvil head assembly 104 in the operative position as discussed in further detail below.

Figure 12:
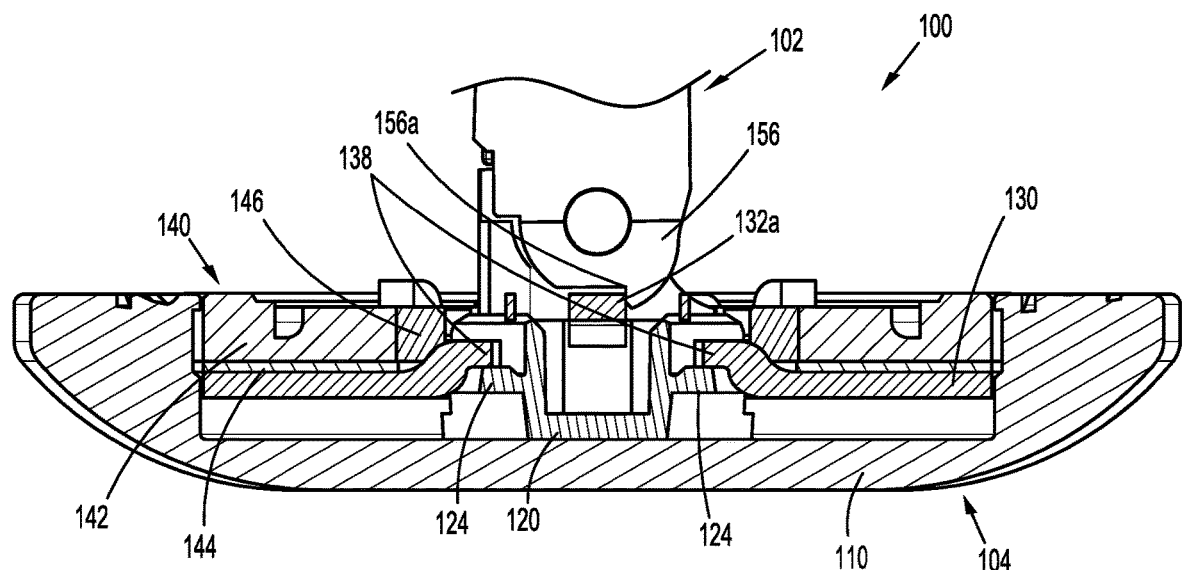
FIG. 12 is a cross-sectional view taken along line 12-12 shown in FIG. 2.
Figure 13:
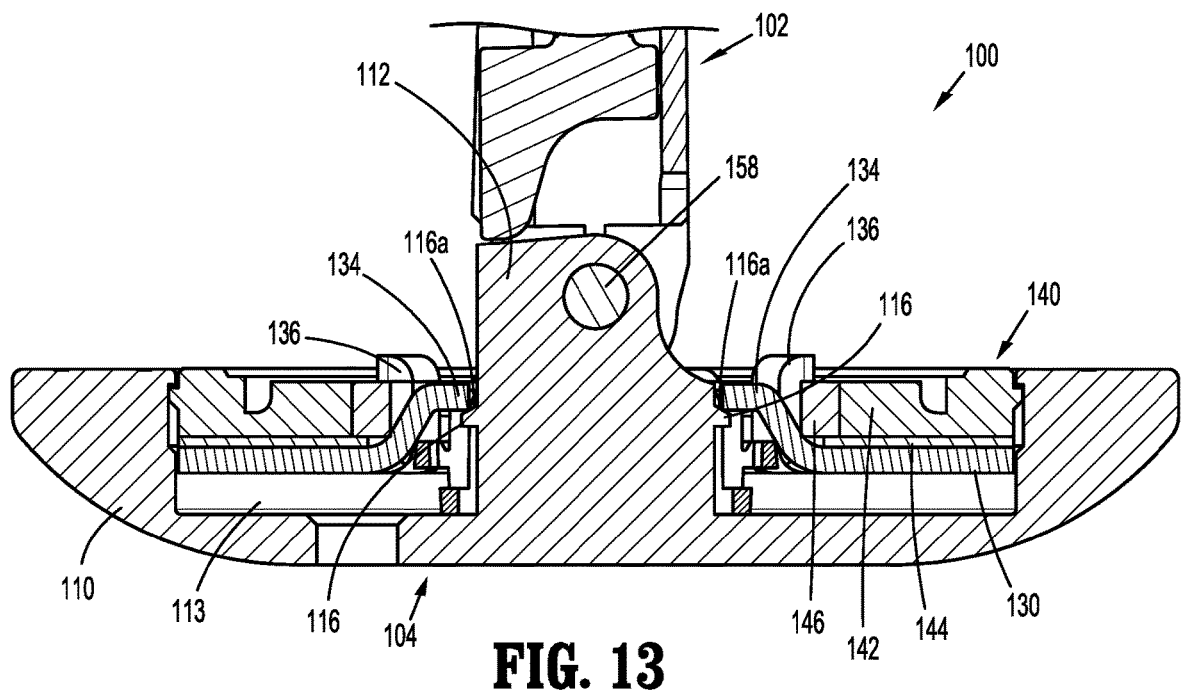
FIG. 13 is a cross-sectional view taken along line 13-13 shown in FIG. 2.

The plunger 152 is urged by the plunger spring 154 into engagement with a proximal end of the post 112 of the anvil head assembly 104 to urge the anvil head assembly 104 about the pivot member 158 towards the tilted position (FIG. 12).

Referring to FIGS. 8-14, prior to firing of the stapling device 10 (FIG. 1), the backup member 130 and the cut ring assembly 140 are in their retracted positions with the cut ring assembly 140 supported about the raised flange 132 of the backup member 130 and secured to the backup member 130 by cut ring retaining features 136. The retainer member 120 is received with the recesses 133 of the raised flange 132 with the plurality of retaining fingers 138 of the backup member 130 engaging the frangible ring 124 of the retainer member 120 to maintain the backup member 130 in the retracted position.

With the backup member 130 in its retracted position, the inwardly extending engagement tabs 132a of the backup member 130 engage the distally facing flats 156a (FIG. 12) of the center rod 150 such that the anvil head assembly 104 is prevented from tilting and is retained in the operative position. As discussed above, the plunger 152 of the center rod assembly 102 is positioned to urge the anvil head assembly 104 about the pivot member 158 towards the tilted position (FIG. 15).

Referring to FIGS. 15-18, when the stapling device 10 (FIG. 1) is approximated and subsequently fired, the annular knife 56 (FIG. 14A) of the shell assembly 50 is advanced from a retracted position recessed within the housing 52 of the shell assembly 50 to an advanced position extending into the cut ring assembly 140 of the anvil head assembly 104. As the annular knife 56 engages the cut ring assembly 140, the force applied to the cut ring assembly 140 by the knife 56 is transferred through the backup member 130 to the frangible ring 124 of the retainer member 120 by the plurality of retaining fingers 138 (FIG. 18) of the backup member 130. The force applied to the cut ring assembly 140 by the knife 56 separates the frangible ring 124 from the body portion 122 of the retainer member 120, thereby releasing the backup member 130 and attached cut ring assembly 140. In this manner, the cut ring assembly 140 and the backup member 130 are advanced from their retracted positions to their advanced positions within the recess 113 (FIG. 16) of the housing 110 of the anvil head assembly 104.

As discussed above, when the backup member 130 moves to its advanced position, the inwardly extending engagement fingers 132a of the backup member 130 are moved to a position spaced from the distally facing flats 156a (FIG. 18) on the distal end of the center rod 150. When the engagement tabs 132a are spaced from the distally facing flats 156a, and the stapling device 10 is moved to the spaced or unapproximated position in relation to the shell assembly 50, the plunger spring 154 (FIG. 17) urges the plunger 152 into the post 112 to urge the anvil head assembly 104 towards the tilted position.

As the backup member 130 is moved to the advanced position, the snap tabs 136 of the backup member 130 engage the angled surfaces 116a of the retaining features 116 of the post 112 and are flexed radially outwardly to permit the snap tabs 136 to pass over the retaining features 116. After passing distally over the retaining features 116, the snap tabs 136 return to a non-flexed condition positioned distally of the and in alignment with the retaining features 116 such that the snap tabs 136 engage the stop surface 116b of the retaining features 116 and are blocked by the retaining features 116 to retain the backup member 130 and the attached cut ring assembly 140 in their advanced positions.

Subsequent to stapling tissue with the anvil assembly 100, the surgical stapling procedure may be completed as described in the '132 patent.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
a center rod assembly including an anvil center rod defining a longitudinal axis and having a proximal portion and a distal portion; and
an anvil head assembly pivotally secured to the distal portion of the anvil center rod, the anvil head assembly including a housing, a backup member, a cut ring assembly, and a retainer member, the housing defining a recess and including a post centrally disposed within the recess, the anvil head assembly being pivotal in relation to the anvil center rod from an operative position in which the longitudinal axis of the anvil center rod is aligned with a longitudinal axis of the post to a tilted position in which the longitudinal axis of the anvil center rod and the longitudinal axis of the post define an acute angle, the backup member and cut ring assembly being supported about the post and movable between retracted and advanced positions, the retainer member being positioned about the post to retain the backup member in its retracted position until a predetermined force is applied to the retainer member by the backup member, the retainer member including a frangible portion and a body portion, wherein separation of the frangible portion from the body portion permits the backup member to move from its retracted position to its advanced position, wherein in its retracted position, the backup member is positioned to engage the center rod to retain the anvil head assembly in the operative position, and in its advanced position, the backup member is positioned to permit pivotal movement of the anvil head assembly to the tilted position, wherein the backup member is configured to engage the housing when the backup member is in the advanced position to retain the cut ring assembly in its advanced position.

2. The anvil assembly of claim 1, wherein the housing includes a tissue contact surface defining a plurality of staple deforming pockets.

3. The anvil assembly of claim 1, wherein the backup member includes retaining features for securing the cut ring assembly to the backup member.

4. The anvil assembly of claim 3, wherein proximal facing surfaces of the retaining features are tapered to facilitate passage of the snap tabs over the retaining features as the backup member moves to its advanced position.

5. The anvil assembly of claim 4, wherein distal facing surfaces of the retaining features form a stop surface configured to engage the snap tabs of the backup member to retain the backup member in its advanced position.

6. The anvil assembly of claim 1, wherein the post defines opposed retaining features and the backup member includes opposed snap tabs, the snap tabs engaging the opposed retaining features when the backup member is in the advanced position to secure the backup member in the advanced position.

7. The anvil assembly of claim 1, wherein the backup member includes a plurality of fingers that engage the frangible portion of the retainer member.

8. The anvil assembly of claim 1, wherein the backup member includes raised flanges, the cut ring assembly being securely supported about the raised flanges.

9. The surgical stapling device of claim 8, wherein the cut ring assembly includes an inner sleeve and a body, the inner sleeve and the body each defining a central opening, the inner sleeve being secured within the central opening of the body, wherein the central opening of the inner sleeve is dimensioned to receive the raised flanges of the backup member.

10. The surgical stapling device of claim 9, wherein the cut ring assembly includes a base member that is positioned between a proximal surface of the body and a distal surface of the backup member.

11. The anvil assembly of claim 1, wherein the center rod assembly includes a plunger and a plunger spring, the plunger spring being positioned to urge the plunger towards the anvil head assembly to urge the anvil head assembly from the operative position towards the tilted position.

12. The anvil assembly of claim 1, wherein the backup member includes a pair of opposed engagement tabs positioned to engage the distal portion of the anvil center rod when the backup member is in its retracted position.

13. The surgical stapling device of claim 12, wherein the anvil center rod includes a pair of spaced arms each having a distally facing flat, the distally facing flats being positioned to engage the opposed engagement tabs of the backup member when the backup member is in its retracted position.

14. The surgical stapling device of claim 1, wherein the backup member is formed of metal.

15. An anvil assembly comprising:
a center rod assembly including an anvil center rod defining a longitudinal axis and having a proximal portion and a distal portion; and
an anvil head assembly pivotally secured to the distal portion of the anvil center rod, the anvil head assembly including a housing, a backup member, a cut ring assembly, and a retainer member, the housing defining a recess and including a post centrally disposed within the recess, the anvil head assembly being pivotal in relation to the anvil center rod from an operative position in which the longitudinal axis of the anvil center rod is aligned with a longitudinal axis of the post to a tilted position in which the longitudinal axis of the anvil center rod and the longitudinal axis of the post define an acute angle, the backup member and cut ring assembly being supported about the post and movable between retracted and advanced positions, the retainer member including a frangible portion and a body portion, wherein separation of the frangible portion from the body portion permits the backup member to move from its retracted position to its advanced position, wherein the backup member is configured to engage the housing when the backup member is in the advanced position to retain the cut ring assembly in its advanced position.

16. The anvil assembly of claim 15, wherein the backup member includes retaining features for securing the cut ring assembly to the backup member.

17. The anvil assembly of claim 16, wherein proximal facing surfaces of the retaining features are tapered to facilitate passage of the snap tabs over the retaining features as the backup member moves to its advanced position.

18. The anvil assembly of claim 15, wherein the post defines opposed retaining features and the backup member includes opposed snap tabs, the snap tabs engaging the opposed retaining features when the backup member is in the advanced position to secure the backup member in the advanced position.

* * * * *